(12) United States Patent
Park et al.

(10) Patent No.: US 12,114,963 B2
(45) Date of Patent: *Oct. 15, 2024

(54) APPARATUS AND METHOD FOR ESTIMATING BIO-INFORMATION

(71) Applicant: SAMSUNG ELECTRONICS CO., LTD., Suwon-si (KR)

(72) Inventors: Sang Yun Park, Hwaseong-si (KR); Hye Rim Lim, Suwon-si (KR); Jin Woo Choi, Suwon-si (KR); Jae Min Kang, Seoul (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 273 days.

This patent is subject to a terminal disclaimer.

(21) Appl. No.: 17/136,150

(22) Filed: Dec. 29, 2020

(65) Prior Publication Data

US 2022/0039666 A1    Feb. 10, 2022

(30) Foreign Application Priority Data

Aug. 5, 2020  (KR) .................. 10-2020-0097919

(51) Int. Cl.
*A61B 5/0205*     (2006.01)
*A61B 5/00*       (2006.01)
(Continued)

(52) U.S. Cl.
CPC ........ *A61B 5/0205* (2013.01); *A61B 5/02007* (2013.01); *A61B 5/165* (2013.01);
(Continued)

(58) Field of Classification Search
CPC ... A61B 5/0205; A61B 5/02007; A61B 5/442; A61B 5/6843; A61B 5/742; A61B 5/02108; A61B 5/02225; A61B 5/02116
See application file for complete search history.

(56) References Cited

U.S. PATENT DOCUMENTS 10,398,324 B2    9/2019  Mukkamala et al.
2008/0082011 A1  4/2008  Chen
(Continued)

FOREIGN PATENT DOCUMENTS

KR    10-2017-0040034 A    4/2017

OTHER PUBLICATIONS

Anand Chandrasekhar et al., "Smartphone-based blood pressure monitoring via the oscillometric finger-pressing method", Sci Transl Med., Mar. 7, 2018, vol. 10, No. 431, pp. 1-24 (24 pages total).

(Continued)

*Primary Examiner* — Michael W Kahelin
*Assistant Examiner* — Moussa Haddad
(74) *Attorney, Agent, or Firm* — Sughrue Mion, PLLC

(57) ABSTRACT

An apparatus for non-invasively measuring bio-information is provided. The apparatus for estimating bio-information may include a pulse wave sensor including a plurality of channels, and configured to measure pulse wave signals at a plurality of points of an object; and a processor configured to generate oscillograms corresponding to the plurality of channels based on the pulse wave signals measured by the plurality of channels; determine a channel, from among the plurality of channels, for estimating the bio-information based on the oscillograms; and estimate the bio-information based on an oscillogram of the channel.

13 Claims, 15 Drawing Sheets

(51) Int. Cl.
*A61B 5/02* (2006.01)
*A61B 5/021* (2006.01)
*A61B 5/16* (2006.01)

(52) U.S. Cl.
CPC ............ *A61B 5/442* (2013.01); *A61B 5/6843* (2013.01); *A61B 5/742* (2013.01); *A61B 5/02108* (2013.01)

(56) References Cited

U.S. PATENT DOCUMENTS

| | | | |
|---|---|---|---|
| 2009/0018453 A1* | 1/2009 | Banet | A61B 5/14551 |
| | | | 600/493 |
| 2013/0079606 A1 | 3/2013 | McGonigle et al. | |
| 2013/0303923 A1 | 11/2013 | Lerner et al. | |
| 2017/0095168 A1 | 4/2017 | Kwon et al. | |
| 2018/0035903 A1 | 2/2018 | Shi et al. | |
| 2019/0069784 A1 | 3/2019 | Mukkamala et al. | |
| 2019/0076032 A1* | 3/2019 | Park | A61B 5/6885 |
| 2019/0269334 A1* | 9/2019 | Addison | G06F 17/11 |
| 2020/0000350 A1 | 1/2020 | Lin et al. | |
| 2020/0008693 A1 | 1/2020 | Mukkamala et al. | |
| 2021/0093211 A1* | 4/2021 | Gbati, I | A61B 5/02427 |
| 2022/0104714 A1* | 4/2022 | Park | A61B 5/02007 |

OTHER PUBLICATIONS

Tuukka Panula et al., "An Automated Device for Recording Peripheral Arterial Waveform" IEEE, Feb. 24, 2020, p. 1 (1 page total).

\* cited by examiner

APPARATUS AND METHOD FOR ESTIMATING BIO-INFORMATION

CROSS-REFERENCE TO RELATED APPLICATION(S)

This application is based on and claims priority under 35 U.S.C. § 119 to Korean Patent Application No. 10-2020-0097919, filed on Aug. 5, 2020, in the Korean Intellectual Property Office, the disclosure of which is incorporated by reference herein in its entirety.

BACKGROUND

1. Field

The following description relates to an apparatus and method for estimating bio-information, and more particularly to technology for extracting cardiovascular characteristics without using a cuff.

2. Description of Related Art

General techniques for extracting cardiovascular characteristics, such as blood pressure, and the like, without using a pressure cuff include a pulse wave analysis (PWA) method and a pulse transit time (PTT) method.

The PWA method is a method of extracting cardiovascular characteristics by analyzing the shape of a photoplethysmography (PPG) signal or a body surface pressure signal obtained from a peripheral part of the body, e.g., a fingertip, a radial artery, or the like. The blood ejected from the left ventricle causes reflection at areas of large branches, such as the renal arteries and the iliac arteries, and the reflection affects the shape of the pulse wave or body pressure wave measured at the peripheral part of the body. Thus, by analyzing this shape, arterial stiffness, arterial age, aortic artery pressure waveform of the like can be inferred.

The PTT method is a method of extracting cardiovascular characteristics, such as arterial stiffness, blood pressure, or the like, by measuring a pulse wave transmission time. In this method, a delay (a PTT) between an R-peak (left ventricular contraction interval) of an electrocardiogram (ECG) and a peak of a PPG signal of a finger or the radial artery is measured by measuring the ECG and PPG signals of the peripheral part of the body and by calculating a velocity at which the blood from the heart reaches the peripheral part of the body by dividing an approximate length of the arm by the PTT.

SUMMARY

Additional aspects will be set forth in part in the description which follows and, in part, will be apparent from the description, or may be learned by practice of the presented embodiments.

According to an aspect of an example embodiment, an apparatus for estimating bio-information may include a pulse wave sensor including a plurality of channels, and configured to measure pulse wave signals at a plurality of points of an object; and a processor configured to generate oscillograms corresponding to the plurality of channels based on the pulse wave signals measured by the plurality of channels; determine a channel, from among the plurality of channels, for estimating the bio-information based on the oscillograms; and estimate the bio-information based on an oscillogram of the channel.

The pulse wave sensor may include a plurality of light sources configured to emit light onto the object; and a plurality of light receivers respectively disposed at predetermined distances from the plurality of light sources, and configured to detect light scattered or reflected from the object.

The plurality of light receivers may comprise at least one of a photodiode array and a complementary metal-oxide semiconductor (CMOS) image sensor.

In response to light of a plurality of wavelengths being emitted from each channel, the processor may generate the oscillograms by subtracting a second oscillogram for a second pulse wave signal of a second wavelength from a first oscillogram for a first pulse wave signal of a first wavelength.

The processor may determine a difference coefficient for the first wavelength and the second wavelength; apply the difference coefficient to the second oscillogram; and subtract the second oscillogram from the first oscillogram based on applying the difference coefficient to the second oscillogram.

The processor may obtain an estimated mean arterial pressure (MAP) values corresponding to the plurality of channels based on the oscillograms; and determine the channel based on the estimated MAP values.

The processor may determine a predetermined number of channels in an order of magnitude of the MAP values.

The processor may exclude an oscillogram of a channel, which does not satisfy predetermined criteria, from the oscillograms; and determine the channel based on remaining oscillograms of remaining channels.

The apparatus may include a force sensor configured to measure a contact force exerted between the object and the pulse wave sensor while the pulse wave signals are measured.

The apparatus may include an area sensor configured to measure a contact area when the object increases or decreases a pressing force applied to the pulse wave sensor.

The processor may control an output interface to output information that guides a contact pressure between the object and the pulse wave sensor while the pulse wave signals are measured.

The bio-information may include one or more of blood pressure, vascular age, arterial stiffness, aortic pressure waveform, vascular compliance, stress index, fatigue level, skin age, and skin elasticity.

According to an aspect of an example embodiment, a method of estimating bio-information may include measuring, by a pulse wave sensor including a plurality of channels, pulse wave signals at a plurality of points of an object; generating oscillograms corresponding to the plurality of channels based on the pulse wave signals measured by the plurality of channels; determining a channel, from among the plurality of channels, for estimating the bio-information based on the oscillograms; and estimating the bio-information based on an oscillogram of the channel.

The generating of the oscillograms may include, in response to light of a plurality of wavelengths being emitted from each channel, generating the oscillograms by subtracting a second oscillogram for a second pulse wave signal of a second wavelength from a first oscillogram for a first pulse wave signal of a first wavelength.

The generating of the oscillograms of each channel may include determining a difference coefficient for the first wavelength and the second wavelength, applying the difference coefficient to the second oscillogram, and subtracting the second oscillogram from the first oscillogram.

The determining of the optimal channel may include obtaining estimated mean arterial pressure (MAP) values corresponding to the plurality of channels based on the oscillograms, and determining the channel based on the estimated MAP values.

The method may include determining a predetermined number of channels in an order of magnitude of the estimated MAP values.

The determining of the channel may include excluding an oscillogram of a channel, which does not satisfy predetermined criteria, from the oscillograms, and determining the channel based on remaining oscillograms of remaining channels.

The method may include obtaining a contact pressure between the object and the pulse wave sensor while the pulse wave signals are measured.

According to an aspect of an example embodiment, an apparatus for estimating final bio-information may include a pulse wave sensor including a plurality of channels, and configured to measure pulse wave signals at a plurality of points of an object; and a processor configured to generate oscillograms corresponding to the plurality of channels based on the pulse wave signals measured by the plurality of channels; estimate bio-information for each channel based on the oscillograms; and estimate the final bio-information by combining the bio-information for each channel

BRIEF DESCRIPTION OF THE DRAWINGS

The above and other aspects, features, and advantages of certain embodiments of the present disclosure will be more apparent from the following description taken in conjunction with the accompanying drawings, in which.

DETAILED DESCRIPTION

Figure 1:
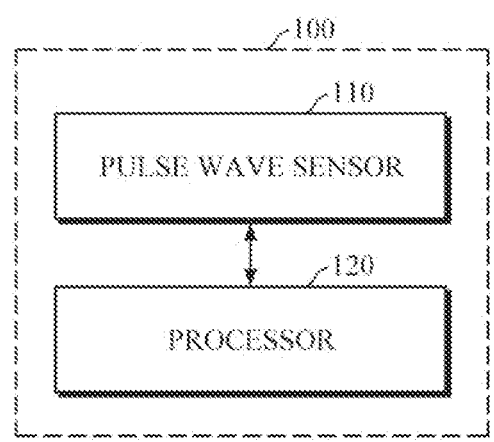
FIG. 1 is a block diagram illustrating an apparatus for estimating bio-information according to an embodiment of the present disclosure.

Details of example embodiments are included in the following detailed description and drawings. Advantages and features of the present disclosure, and a method of achieving the same will be more clearly understood from the following embodiments described in detail with reference to the accompanying drawings. Throughout the drawings and the detailed description, unless otherwise described, the same drawing reference numerals will be understood to refer to the same elements, features, and structures.

It will be understood that, although the terms "first," "second," etc. may be used herein to describe various elements, these elements should not be limited by these terms. These terms are only used to distinguish one element from another. Also, the singular forms of terms are intended to include the plural forms of the terms as well, unless the context clearly indicates otherwise. It will be further understood that when an element is referred to as "comprising" another element, the element is intended not to exclude one or more other elements, but to further include one or more other elements, unless explicitly described to the contrary. In the following description, terms such as "unit" and "module" indicate a unit for processing at least one function or operation and the unit may be implemented by using hardware, software, or a combination thereof.

Hereinafter, embodiments of an apparatus and method for estimating bio-information will be described in detail with reference to the accompanying drawings.

Figure 2A:
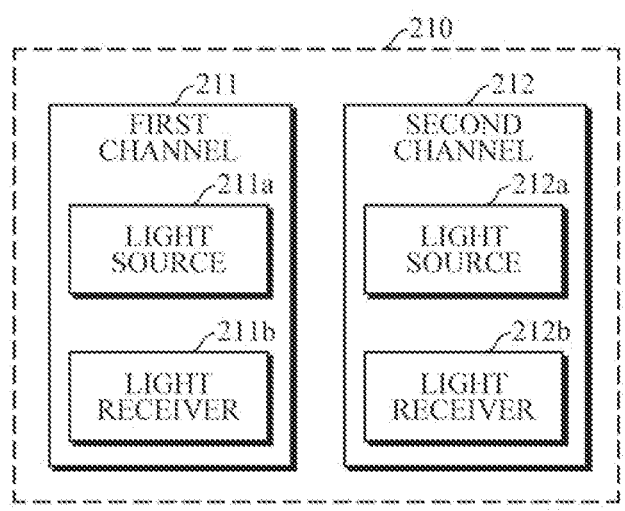
FIGS. 2A to 2C are diagrams illustrating examples of a configuration of a pulse wave sensor of an apparatus for estimating bio-information.
Figure 2B:
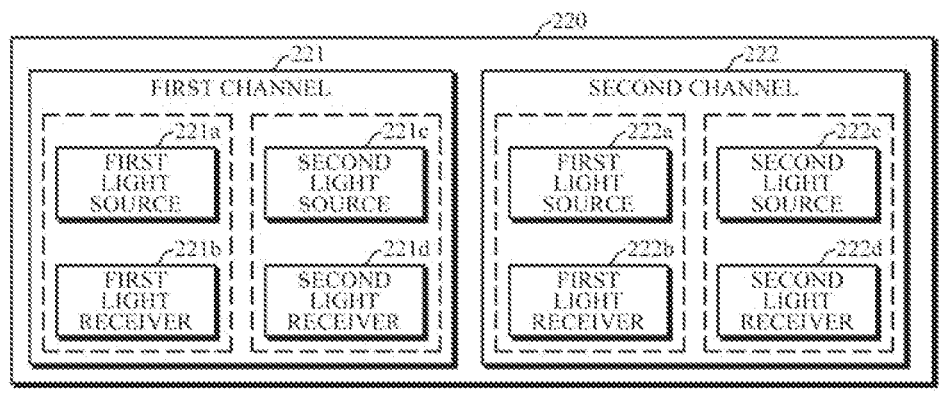
Figure 2C:
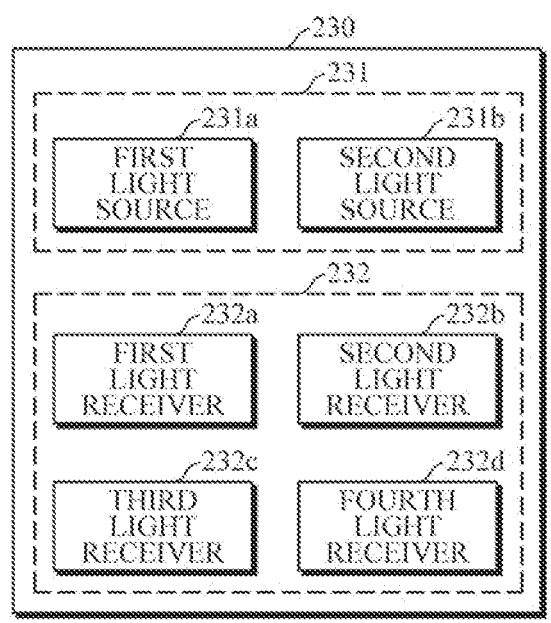

FIG. 1 is a block diagram illustrating an apparatus for estimating bio-information according to an embodiment of the present disclosure. FIGS. 2A to 2C are diagrams illustrating examples of a configuration of a pulse wave sensor of an apparatus for estimating bio-information.

The apparatus 100 for estimating bio-information according to the embodiment may be embedded in a terminal, such as a smartphone, a tablet personal computer (PC), a desktop computer, a laptop computer, and the like, or may be manufactured as an independent hardware device. In this case, when manufactured as an independent hardware device, the device may be implemented as a wearable device worn on an object OBJ so that a user may easily measure bio-information while carrying the device. Examples of the wearable device may include a wristwatch-type wearable device, a bracelet-type wearable device, a wristband-type wearable device, a ring-type wearable device, a glasses-type wearable device, a headband-type wearable device, or the like, but the wearable device is not limited thereto, and may be modified for various purposes, such as a fixed type device and the like used in medical institutions for measuring and analyzing bio-information.

Referring to FIG. 1, the apparatus 100 for estimating bio-information includes a pulse wave sensor 110 and a processor 120.

The pulse wave sensor 110 measures a photoplethysmography (PPG) signal (hereinafter referred to as a "pulse wave signal") from an object. In this case, the object may be a body area which may come into contact with the pulse wave sensor 110, and may be a body part at which pulse waves may be easily measured based on PPG signals. For example, the object may be a finger where blood vessels are densely located, but the object is not limited thereto and may be an area on the wrist that is adjacent to the radial artery, or a peripheral part of the body, such as an upper portion of the wrist, toes, etc., where veins or capillaries are located.

The pulse wave sensor 110 may include a plurality of light sources for emitting light onto the object, and one or more light receivers which are disposed at positions spaced apart from the light sources by a predetermined distance and detect light scattered or reflected from the object. At least some of the light sources may emit light of different wavelengths. The light sources may include a light emitting diode (LED), a laser diode (LD), a phosphor, etc., but are not limited thereto. Further, the light receivers may include a photodiode, a photodiode array, a complementary metal-oxide semiconductor (CMOS) image sensor, a charge-coupled device (CCD) image sensor, and the like.

The pulse wave sensor 110 may have multiple channels to measure a plurality of pulse wave signals at multiple points of the object. The channels of the pulse wave sensor 110 may be arranged in a predetermined shape such as a circular shape, an oval shape, a linear shape, etc., so as to measure pulse wave signals at multiple points of the object. Each channel of the pulse wave sensor 110 may include one or more light sources and one or more light receivers, which may be shared by two or more channels. Further, each channel may include two or more light sources to emit light of a plurality of wavelengths.

Referring to FIG. 2A, a pulse wave sensor 210 according to an embodiment may have a first channel 211 for measuring a pulse wave signal at a first point of the object, and a second channel 212 for measuring a pulse wave signal at a second point of the object. For convenience of explanation, FIG. 2A illustrates two channels 211 and 212, but the pulse wave sensor 210 is not limited thereto and may include various numbers of channels according to the size and shape of a form factor, and the like.

The first channel 211 may include one light source 211a and one light receiver 211b. Likewise, the second channel 212 may include one light source 212a and one light receiver 212b. For example, the light sources 211a and 212a and the light receivers 211b and 212b of the respective channels 211 and 212 may have a size in a range of 3 mm to 10 mm.

The light source 211a of the first channel 211 and the light source 212a of the second channel 212 may emit light of the same wavelength. For example, the light sources 211a and 212a may emit light of an infrared wavelength, a green wavelength, a blue wavelength, a red wavelength, a white wavelength, and the like. However, the light sources 211a and 212a are not limited thereto, and may emit light of different wavelengths. In this case, the light sources 211a and 212a may emit light of a single wavelength. The respective channels 211 and 212 of the pulse wave sensor 210 may have a color filter, provided on a front surface of the light sources 211a and 212a or the light receivers 211b and 212b, to pass or detect two or more wavelengths.

Referring to FIG. 2B, a pulse wave sensor 220 according to another embodiment may have a first channel 221 and a second channel 222 for measuring pulse wave signals at multiple points of the object. For convenience of explanation, FIG. 2B illustrates two channels 221 and 222, but the pulse wave sensor 220 is not limited thereto.

The first channel 221 may include a plurality of light sources 221a and 221c and a plurality of light receivers 221b and 221d. Each of the light sources 221a and 221c may emit light of different wavelengths. For example, the light sources 221a and 221c may emit light of an infrared wavelength, a green wavelength, a blue wavelength, a red wavelength, and the like. The number of the light receivers is not particularly limited, and the first channel 221 may include, for example, one light receiver which may be shared by the first light source 221a and the second light source 221c. Likewise, the second channel 222 may include a plurality of light sources 222a and 222c and a plurality of light receivers 222b and 222d, and each of the light sources 222a and 222c may emit light of different wavelengths. The number of the light receivers is not particularly limited.

Referring to FIG. 2C, a pulse wave sensor 230 according to yet another embodiment may have a plurality of light sources 231a and 231b formed in a linear shape, a circular shape, a rectangular shape, etc., in a first area 231 of the pulse wave sensor 230. Each of the light sources 231a and 231b may emit light of different wavelengths. Further, a plurality of light receivers 232a, 232b, 232c, and 232d may be disposed in a second area 232 at a predetermined distance from the first area 231 of the pulse wave sensor 230. In order to detect pulse wave signals at multiple points of the object, the light receivers 232a, 232b, 232c, and 232d may be disposed at positions corresponding to the respective multiple points of the object, and may be formed in in a linear shape, a circular shape, a rectangular shape, and the like.

For convenience of explanation, FIG. 2C illustrates two light sources 231a and 231b and four light receivers 232a, 232b, 232c, and 232d, but the number of the light sources and the light receivers is not particularly limited. The light sources and the light receivers may be provided in the same number or in different numbers. In order to detect pulse wave signals at multiple points of the object, a plurality of channels may be pre-defined as a combination of one or more light sources and one or more light receivers.

Various embodiments of the structure of the pulse wave sensor 110 of FIG. 1 are described above with reference to FIGS. 2A to 2C. However, these are merely examples, and the structure is not particularly limited to the above examples, and in order to detect pulse wave signals at multiple points of the object, various numbers and arrangements of the channels, light sources, and light receivers may be provided according to the position of the object, the size and shape of a form factor, and the like.

Referring to FIG. 1, the processor 120 may sequentially or simultaneously control each of the channels in a time division manner. Further, if each channel includes a plurality of light sources of different wavelengths, the processor 120 may drive the light sources in the order from short to long wavelengths, or vice versa. In this case, driving conditions of the light sources, e.g., a driving sequence and a current strength of light sources, a pulse duration, etc., may be pre-defined.

In addition, the processor 120 may estimate bio-information by using pulse wave signals measured at multiple points of the object by the respective channels of the pulse wave sensor 110. In this case, the bio-information may include blood pressure, vascular age, arterial stiffness, aortic pressure waveform, skin elasticity, skin age, stress index, fatigue level, etc., but is not limited thereto. For convenience of explanation, the following description will be given using blood pressure as an example.

The processor 120 may obtain an oscillogram from the pulse wave signal of each channel. As will be described later, the processor 120 may generate an oscillogram based on a relationship between a change in contact pressure applied by the object to the pulse wave sensor 110 and a change in amplitude of the pulse wave signal of each channel.

In the case where each channel includes a plurality of light sources having different wavelengths, the processor 120 may generate oscillograms for each wavelength based on the pulse wave signals for each wavelength of each channel, and may generate a representative oscillogram of each channel by subtracting the oscillograms for each wavelength. For example, in order to subtract a first oscillogram of a first wavelength and a second oscillogram of a second wavelength, the processor 120 may first determine a difference coefficient for normalizing the first oscillogram and the second oscillogram. Then, based on applying the determined difference coefficient to the second oscillogram, the processor 120 may normalize the first oscillogram and the second oscillogram and may subtract the second oscillogram from the first oscillogram. In this case, the first wavelength may be a relatively long wavelength, and the second wavelength may be a relatively short wavelength. In this case, the processor 120 may determine the difference coefficient for normalization by normalizing an amplitude of the oscillogram for each wavelength or by applying an absorbance-based model generated using the Beer-Lambert Law.

Based on obtaining the oscillograms of each channel, the processor 120 may exclude a channel which does not satisfy predetermined criteria. For example, if a full width at half maximum (FWHM) between a contact pressure at an onset point and a contact pressure at a half-maximum point of the oscillogram is greater than or equal to a predetermined threshold value, the processor 120 may exclude a corresponding channel. Alternatively, if a width at a point corresponding to a predetermined ratio between the onset point and the maximum point of the oscillogram is greater than or equal to a predetermined threshold value, or if a statistical value, e.g., a sum total, a mean value, a median value, and the like, of residuals between an actual pulse wave amplitude at a point corresponding to a predetermined contact pressure value and a pulse wave amplitude of the oscillogram after curve fitting is greater than or equal to a predetermined threshold value, the processor 120 may exclude a corresponding channel. However, the present disclosure is not limited thereto.

The processor 120 may estimate blood pressure, e.g., mean arterial pressure (MAP), systolic blood pressure (SBP), and diastolic blood pressure (DBP), by using the oscillograms of each channel. Based on generating the oscillograms from the pulse wave signals of each channel, the processor 120 may determine an optimal channel, and may estimate blood pressure by using the oscillogram of the determined channel.

For example, the processor 120 may determine an optimal channel based on an amplitude of an alternating current (AC) component of the pulse wave signal of each channel, e.g., based on a maximum pulse wave amplitude and/or a magnitude of MAP estimated by using the oscillograms of each channel. For example, the processor 120 may determine a channel, having a maximum amplitude of the AC component of the pulse wave signal or having a maximum estimated MAP value, as the optimal channel. Alternatively, the processor 120 may determine an optimal channel by combining other conditions. For example, based on an amplitude of the AC component and/or a magnitude of the estimated MAP value, the processor 120 may determine an optimal channel among the channels disposed within a predetermined distance from the center of the pulse wave sensor 110. Further, if an amplitude of the AC component of the pulse wave signal is greater than or equal to a predetermined threshold, or in the order of amplitude of the AC component, the processor 120 may determine an optimal channel, having a maximum estimated MAP value, among a predetermined number of channels. However, the optimal channel is not limited thereto, and various conditions may be set for determining the optimal channel.

Alternatively, the processor 120 may estimate blood pressure for each channel by using oscillograms of all the channels of the pulse wave sensor 110 or two or more channels selected therefrom, and may estimate a final blood pressure by combining the estimated blood pressure values for each channel. In this case, as described above, the processor 120 may select a predetermined number of channels in the order of amplitude of the AC component of the pulse wave signals and/or in the order of magnitude of the estimated MAP values of all the channels. Further, the processor 120 may determine a channel, having a maximum amplitude of the AC component of the pulse wave signal and a maximum estimated MAP, as an optimal channel.

Based on obtaining, e.g., MAP, SBP, and DBP for each channel, the processor 120 may determine a statistical value, e.g., a mean value or a median value, of the obtained MAP values, or a statistical value of SBP values and a statistical value DBP values as a final MAP, a final SBP, and a final DBP. However, the final blood pressure values are not limited thereto, and may be obtained by using a pre-defined linear or non-linear combination equation. In this case, the processor 120 may combine the values by applying different weights to the values in the order of amplitude of the AC component of the pulse wave signal or in the order of magnitude of the estimated MAP.

Figure 3A:
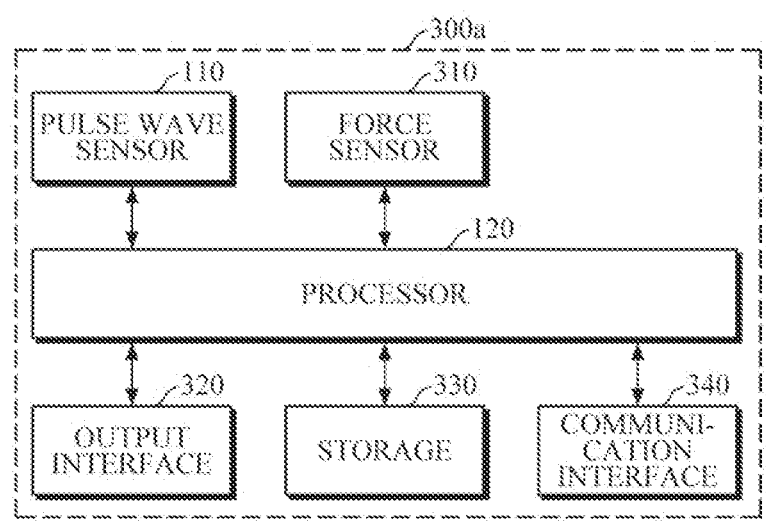
FIGS. 3A and 3B are block diagrams illustrating an apparatus for estimating bio-information according to other embodiments of the present disclosure.
Figure 3B:
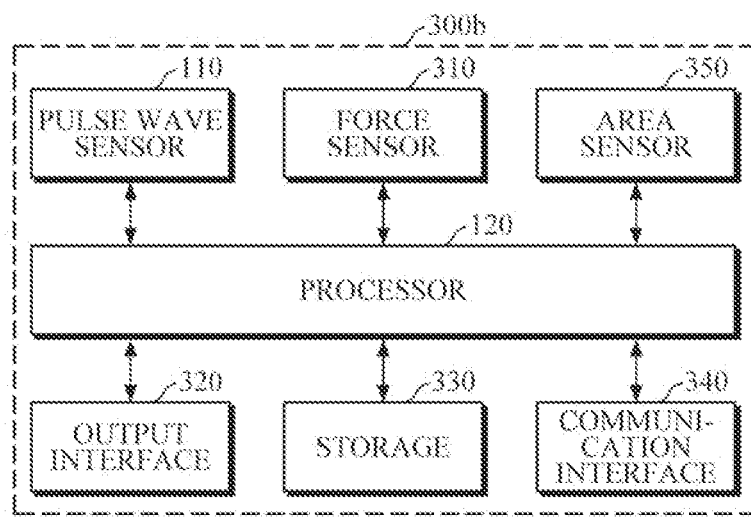

FIGS. 3A and 3B are block diagrams illustrating an apparatus for estimating bio-information according to other embodiments of the present disclosure.

Referring to FIGS. 3A and 3B, the apparatus for estimating bio-information includes the pulse wave sensor 110, the processor 120, a force sensor 310, an output interface 320, a storage 330, and a communication interface 340. The pulse wave sensor 110 and the processor 120 are described above in detail.

When a user places an object on the pulse wave sensor 110 for a predetermined period of time and increases or decreases a pressing force to measure a pulse wave signal, the force sensor 310 may measure a contact force between the object and the pulse wave sensor 110. The force sensor 130 may include a strain gauge, and the like.

The processor 120 may obtain contact pressure between the object and the pulse wave sensor 110 based on the contact force measured by the force sensor 310. For example, the processor 120 may obtain contact pressure based on an area of a contact surface between the pulse wave sensor 110 and the object and the contact force measured by the force sensor 310. In another example, the processor 120 may obtain contact pressure based on the contact force by using a conversion model which defines a correlation between the contact force and the contact pressure.

Further, referring to FIG. 3B, an apparatus 300b for estimating bio-information may further include an area sensor 350. The area sensor 350 may measure a contact area of the object when the object is in contact with the pulse wave sensor 110 and increases or decreases a pressing force. The area sensor 350 may be disposed above or below the pulse wave sensor 110.

The processor 120 may also obtain contact pressure based on the contact force measured by the force sensor 310 and the contact area measured by the area sensor 350.

Based on receiving a request for estimating bio-information from a user, the processor 120 may control the output interface 320 to provide information that guides the user on a contact state. For example, based on receiving the request for estimating bio-information, the processor 120 may obtain, from the storage 330, a reference pressure to be applied by the object to the pulse wave sensor 110, and may control the output interface 320 to provide information that guides the user on the obtained reference pressure. Further, the processor 120 may control the output interface 320 to provide information that guides the user on the contact pressure in real time based on the contact force and/or contact area which are measured in real time by the force sensor 310 and/or the area sensor 350 while the pulse wave signal is measured.

The communication interface 340 may communicate with an external device by using communication techniques under the control of the processor 120, and may receive data for estimating bio-information from the external device or may transmit a processing result of the processor 120 to the external device. In this case, the external device may include a smartphone, a tablet PC, a wearable device, a cuff manometer, and the like.

In this case, examples of the communication techniques may include Bluetooth communication, Bluetooth Low Energy (BLE) communication, Near Field Communication (NFC), wireless local area network (WLAN) communication, Zigbee communication, Infrared Data Association (IrDA) communication, wireless fidelity (Wi-Fi) Direct (WFD) communication, Ultra-Wideband (UWB) communication, Ant+ communication, Wi-Fi communication, Radio Frequency Identification (RFID) communication, 3G communication, 4G communication, 5G communication, and the like. However, this is merely exemplary and is not intended to be limiting.

The output interface 320 may output and provide the pulse wave signal measured by the pulse wave sensor 110 and/or a processing result of the processor 120 to a user. The output interface 320 may provide the information by various visual/non-visual methods using a display module, a speaker, a haptic device, and the like mounted in the apparatus.

For example, the output interface 320 may output the measured pulse wave signal, the oscillogram of each channel, and the like in the form of graphs. Further, the output interface 320 may visually display an estimated bio-information value of a user by using various visual methods, such as by changing color, line thickness, font, and the like, based on whether the estimated blood pressure value falls within or outside a normal range. In addition, the output interface 320 may output the estimated bio-information value by voice, in which case the output interface 320 may also output the information using vibrations, tactility, and the like, based on whether the estimated bio-information value is abnormal or normal, so that the user may easily recognize abnormality in their health condition. Alternatively, based on comparing the estimated bio-information value with a previous estimation history, if it is determined that the estimated bio-information value is abnormal, the output interface 320 may provide a warning message, an alarm signal, and the like, as well as guide information on a user's action such as food information that the user should be careful about, related hospital information, and the like.

The storage 330 may store information, such as a variety of information related to estimating bio-information, the obtained pulse wave signals and oscillograms, the estimated bio-information values, and the like. Further, the storage 330 may store light source driving conditions, a contact pressure conversion model, a blood pressure estimation model, conditions for excluding channels, conditions for determining an optimal channel, and the like. In addition, the storage 330 may store user characteristics information such as a user's age, gender, health condition, and the like. However, the information is not limited thereto.

The storage 330 may include at least one storage medium of a flash memory type memory, a hard disk type memory, a multimedia card micro type memory, a card type memory (e.g., a secure digital (SD) memory, an extreme digital (XD) memory, etc.), a Random Access Memory (RAM), a Static Random Access Memory (SRAM), a Read Only Memory (ROM), an Electrically Erasable Programmable Read Only Memory (EEPROM), a Programmable Read Only Memory (PROM), a magnetic memory, a magnetic disk, and an optical disk, and the like, but is not limited thereto.

Hereinafter, an example of estimating blood pressure by the aforementioned apparatuses 100, 300a, and 300b for estimating bio-information will be described with reference to FIGS. 4A to 6B.

Figure 4A:
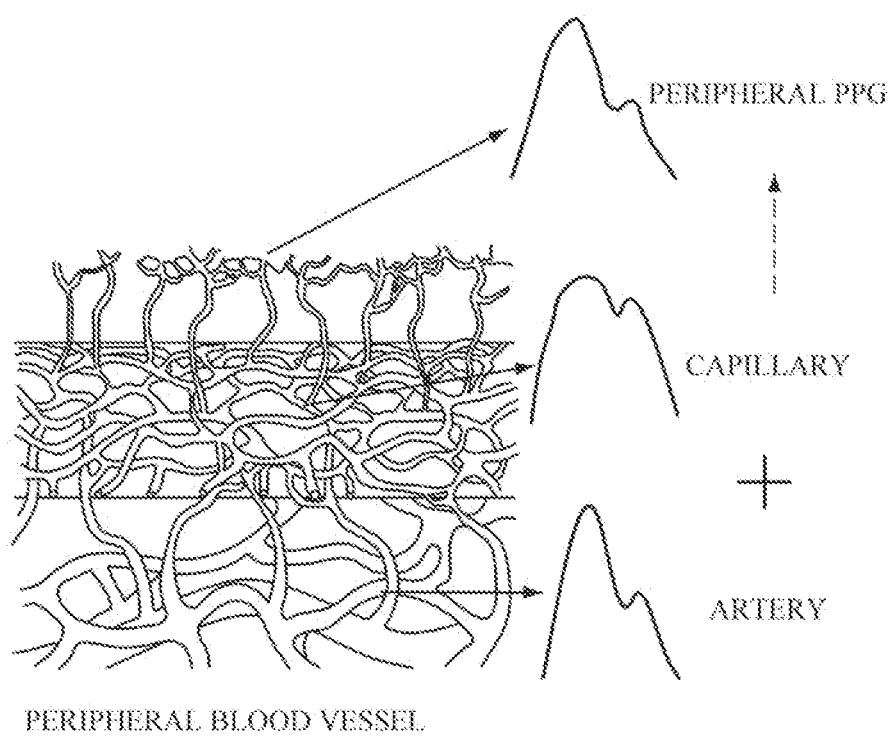
FIGS. 4A and 4B are diagrams explaining an example of generally estimating bio-information.
Figure 4B:
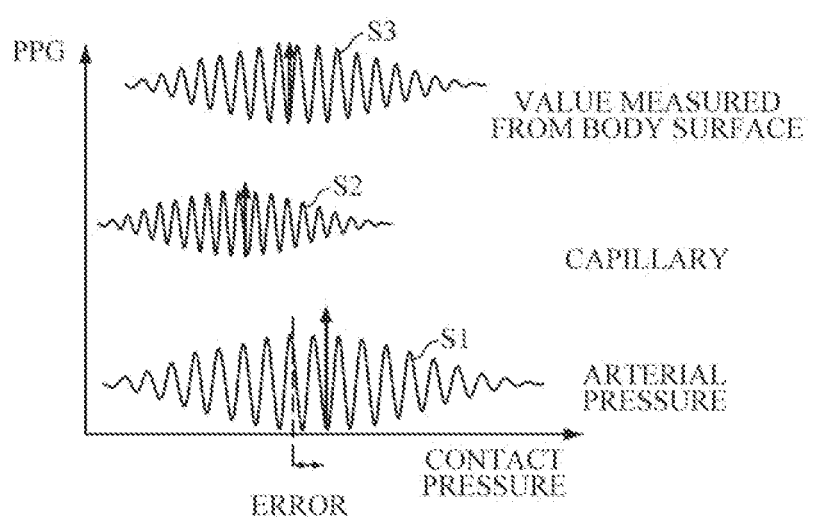

FIGS. 4A and 4B are diagrams explaining an example of generally estimating bio-information.

Referring to FIG. 4A, an apparatus for measuring blood pressure without a cuff generally measures blood pressure by using photoplethysmography (PPG) signals. In this case, a pulse wave sensor comes into contact with a body surface at various pressure levels, and estimates blood pressure by measuring pulse wave signals at each contact pressure level and by obtaining mean arterial pressure (MAP) of local blood vessels. In this case, the PPG signals, measured by the pulse wave sensor from the body surface, may be observed as a combination of arterial pulse wave signals, generated at great depths from the body surface, and capillary pulse wave signals generated at relatively shallow depths from the body surface. Here, the capillary pulse wave signals may act as noise in estimating blood pressure using oscillometry.

Referring to FIG. 4B, a pulse wave signal at the bottom of the graph represents an arterial pulse wave signal S1; a pulse wave signal at the center of the graph represents a capillary pulse wave signal S2; and a pulse wave signal at the top of the graph represents a peripheral pulse wave signal S3 measured from the body surface. As the peripheral pulse wave signal S3 is represented by a combination of the arterial pulse wave signal S1 and the capillary pulse wave signal S2, it can be seen that a maximum amplitude point associated with blood pressure is moved from an arrow point of the arterial pulse wave signal S1 to an arrow point of the peripheral pulse wave signal S3. This shows that accuracy may be reduced when blood pressure is measured using oscillometry. That is, a value measured from the body surface includes an error value added to an arterial blood pressure value, thereby resulting in a difference from accurate blood pressure values.

Figure 5A:
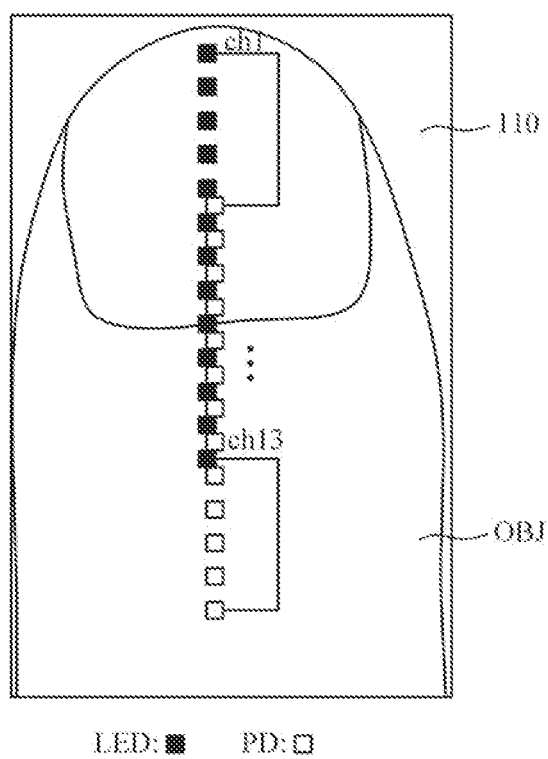
FIGS. 5A and 5B are diagrams explaining an example of measuring multi-channel pulse wave signals.
Figure 5B:
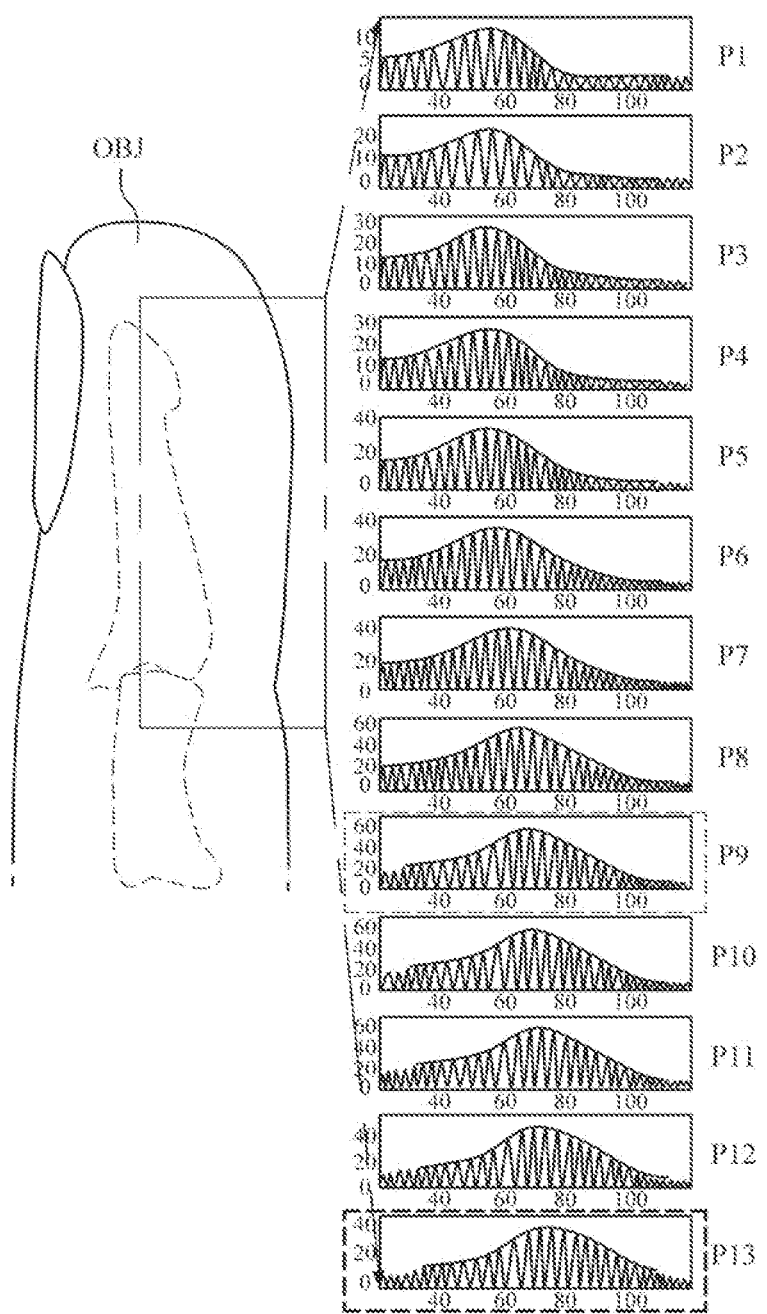
Figure 6A:
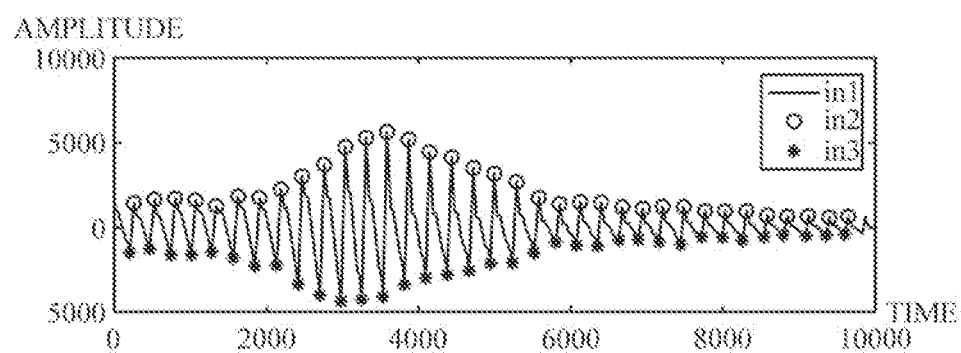
FIGS. 6A and 6B are diagrams explaining an example of estimating bio-information using oscillograms.
Figure 6B:
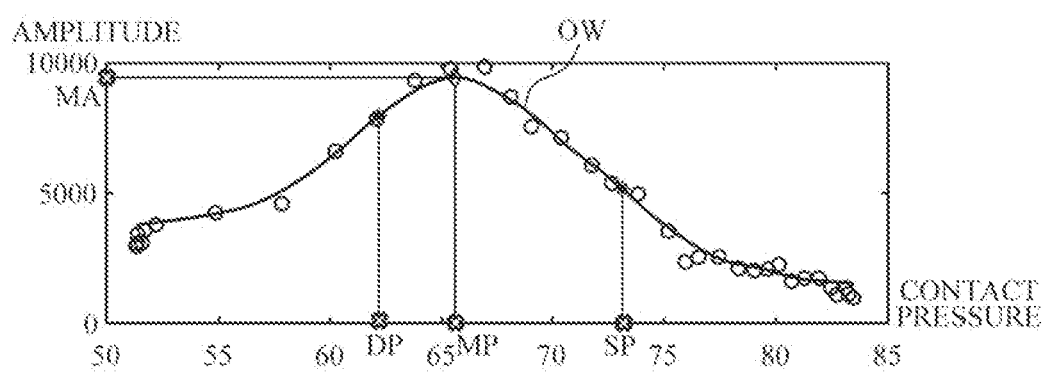

FIGS. 5A and 5B are diagrams explaining an example of measuring multi-channel pulse wave signals. FIGS. 6A and 6B are diagrams explaining an example of estimating bio-information using oscillograms.

FIG. 5A illustrates an example of the pulse wave sensor 110 having an LED array and a photodiode (PD) array which are arranged in a linear shape. As illustrated in FIG. 5A, each of the channels ch1 through ch13 may be arranged in a linear shape to measure pulse wave signals at different points of the object OBJ. Each of the channels ch1 through ch13 includes pairs of LEDs and PDs, which are spaced apart from each other by a predetermined distance.

The processor 120 may obtain pulse wave signals at multiple points of a finger by sequentially driving the pairs of LEDs and PDs of each of the channels ch1 through ch13, and may obtain oscillograms based on the obtained pulse wave signals of the respective channels ch1 through ch13 and contact pressure values.

FIG. 5B illustrates oscillograms of the respective channels ch1 through ch13. The processor 120 may estimate MAP for each channel by using the oscillograms P1 through P13 of the respective channels ch1 through ch13. An example of generating an oscillogram and estimating MAP will be described later with reference to FIGS. 6A and 6B. Further, the processor 120 may select an optimal channel based on a magnitude of MAP. For example, the processor 120 may determine, as an optimal channel, the channel ch13 of the oscillogram P13 having a maximum MAP value. However, determination of the optimal channel is not limited thereto, and the processor 120 may determine, as the optimal channel, a channel of the oscillogram P9 having a maximum amplitude of the AC component of the pulse wave signal, e.g., maximum amplitude of the pulse wave signal. Further, the processor 120 may determine the optimal channel by various methods described above, and may determine the optimal channel by using channels remaining after excluding channels which do not satisfy pre-defined conditions.

Based on determining the channel ch13 as the optimal channel, the processor 120 may estimate systolic blood pressure (SBP) and diastolic blood pressure (DBP) by using the oscillogram P13 of the determined optimal channel, as will be described below. Alternatively, when determining, as the optimal channel, three channels ch13, ch12, and ch11 in the order of magnitude of the estimated MAP, the processor 120 may estimate MAP, SBP, and DBP from the oscillograms P13, P12, and P11, respectively, of the determined optimal channels as will be described below, and may determine a statistical value of MAP values, a statistical value of SBP values, and a statistical value of DBP values of each of the channels as MAP, SBP, and DBP, respectively. In this case, in the order of magnitude of MAP, the processor 120 may apply different weights to the statistical values of MAP, SBP, and DBP, and may obtain weighted statistical values thereof.

An example of generating an oscillogram and estimating MAP, DBP, and SBP based on pulse wave signals will be described below with reference to FIGS. 6A and 6B.

FIG. 6A illustrates an example of a change in amplitude of pulse wave signals measured while an object, being in contact with the pulse wave sensor 110, gradually increases a pressing force on the pulse wave sensor 110. FIG. 6B illustrates an oscillogram OW representing a relationship between a change in contact pressure applied by the object to the pulse wave sensor 110 and the amplitude of a pulse wave signal.

The processor 120 may extract, e.g., a peak-to-peak point of the pulse wave signal waveform by subtracting a negative (−) amplitude value in3 from a positive (+) amplitude value in2 of a waveform envelope in1 at each measurement time of the obtained pulse wave signal, and may obtain the oscillogram (OW) by plotting the peak-to-peak amplitude at each measurement time against the contact pressure value at a corresponding time and by performing, for example, polynomial curve fitting.

The processor 120 may estimate blood pressure by using the generated oscillogram OW. For example, the processor 120 may estimate mean arterial pressure (MAP) based on a contact pressure value MP at a maximum point MA of the pulse wave in the oscillogram. For example, the processor 120 may determine, as MAP, the contact pressure value MP itself at the maximum point of the pulse wave. Alternatively, the processor 120 may estimate MAP by applying the contact pressure value MP to a pre-defined MAP estimation equation. In this case, the MAP estimation equation may be expressed in the form of various linear or non-linear combination functions, such as addition, subtraction, division, multiplication, logarithmic value, regression equation, and the like, with no particular limitation.

Further, the processor 120 may estimate diastolic blood pressure (DBP) and systolic blood pressure (SBP) based on contact pressure values DP and SP at points to the left and right of an amplitude value at the maximum point MA of the pulse wave and having a preset ratio, e.g., 0.5 to 0.7, to the amplitude value at the maximum point MA. Likewise, the processor 120 may also determine the contact pressure values DP and SP as DBP and SBP, respectively. Further, the processor 120 may estimate DBP and SBP by using predefined DBP estimation equation and SBP estimation equation.

Figure 7:
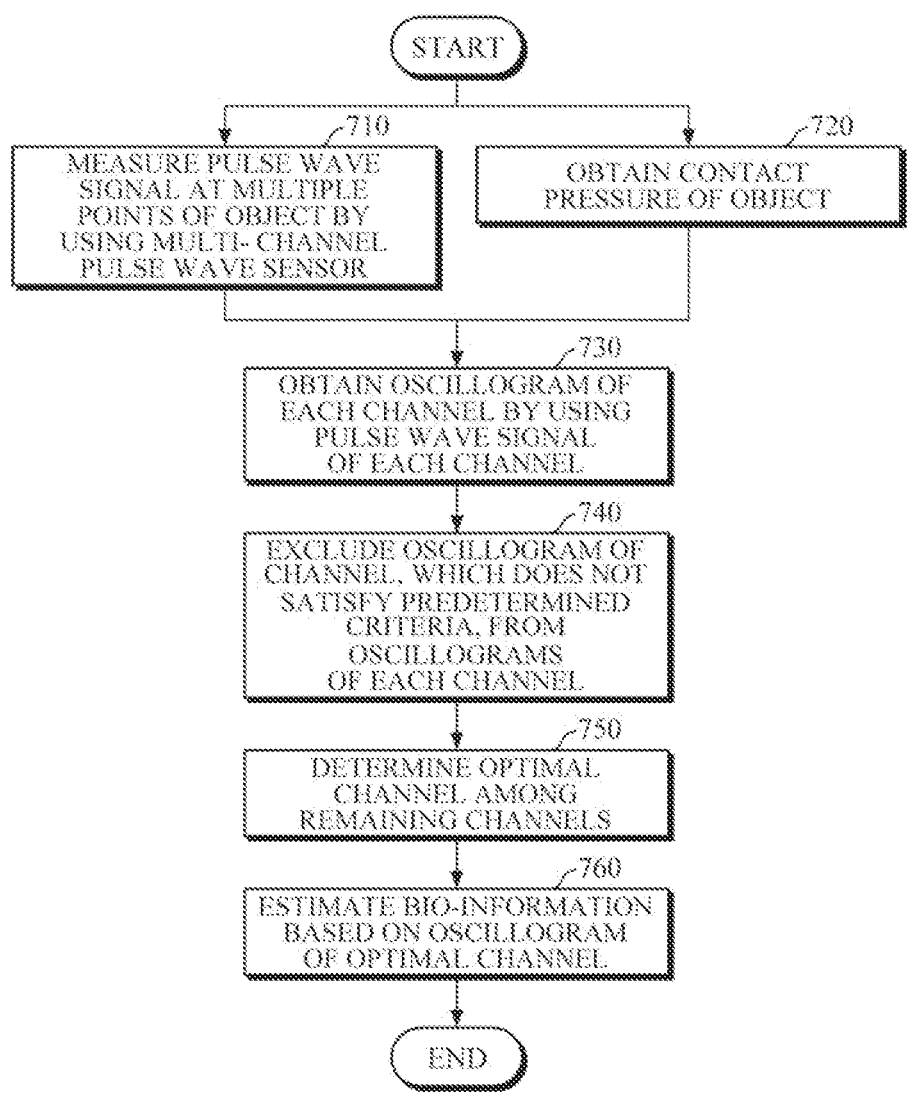
FIG. 7 is a flowchart illustrating a method of estimating bio-information according to an embodiment of the present disclosure.

FIG. 7 is a flowchart illustrating a method of estimating bio-information according to an embodiment of the present disclosure.

The method of FIG. 7 may be an example of a method of estimating bio-information which is performed by the apparatuses 100, 300a, and 300b. Various examples of estimating bio-information are described above in detail, and thus will be described below.

Based on a user placing an object on a multi-channel pulse wave sensor, the apparatus for estimating bio-information may measure a plurality of pulse wave signals at multiple points of the object by using the multi-channel pulse wave sensor in operation 710. The apparatus for estimating bio-information may control the pulse wave sensor based on receiving a request for estimating bio-information from the user or if pre-determined criteria are satisfied. Various examples of the multi-channel pulse wave sensor for measuring pulse wave signals at multiple point of the object are described in detail above.

Then, the apparatus for estimating bio-information may obtain contact pressure between the object and the pulse wave sensor when the object, being in contact with the pulse wave sensor, changes a force applied to the pulse wave sensor in operation 720. As described above, by using a force sensor and/or an area sensor, the apparatus for estimating bio-information may obtain a contact force applied by the object to the pulse wave sensor and/or a contact area between the object and the pulse wave sensor, and may obtain contact pressure based on the obtained contact force and/or contact area.

Subsequently, the apparatus for estimating bio-information may obtain oscillograms of each channel by using the pulse wave signals measured for each channel in operation 730. In this case, if a plurality of pulse wave signals are obtained using a plurality of light sources emitting light of different wavelengths, the apparatus for estimating bio-information may obtain oscillograms from each of the pulse wave signals, and may obtain a representative oscillogram for each channel by subtracting the obtained plurality of oscillograms.

Next, the apparatus for estimating bio-information may exclude an oscillogram of a channel, which does not satisfy predetermined criteria, from the oscillograms of each channel in operation 740. As described above, an FWHM of the pulse wave signal is greater than or equal to a predetermined threshold value, or if a sum of residuals in the oscillogram is greater than or equal to a predetermined threshold value, the apparatus for estimating bio-information may exclude a corresponding channel.

Then, the apparatus for estimating bio-information may determine an optimal channel in operation 750 among the channels remaining after the exclusion in operation 740. For example, the apparatus for estimating bio-information may determine the optimal channel based on an amplitude of an AC component of the pulse wave signal of each channel and/or a magnitude of MAP estimated using the oscillograms.

Subsequently, the apparatus for estimating bio-information may estimate bio-information based on the oscillogram of the determined optimal channel in operation 760. For example, the apparatus for estimating bio-information may determine MAP based on a contact pressure value corresponding to a maximum amplitude value of the oscillogram, and may determine SBP and DBP based on contact pressure values at points corresponding to a predetermined ratio of the maximum amplitude value. Further, if a plurality of optimal channels are determined, the apparatus for estimating bio-information may obtain a statistical value of MAP values, a statistical value of SBP values, and a statistical value of DBP values, obtained from the oscillograms of the respective channels, as a final MAP, a final SBP, and a final DBP.

Figure 8:
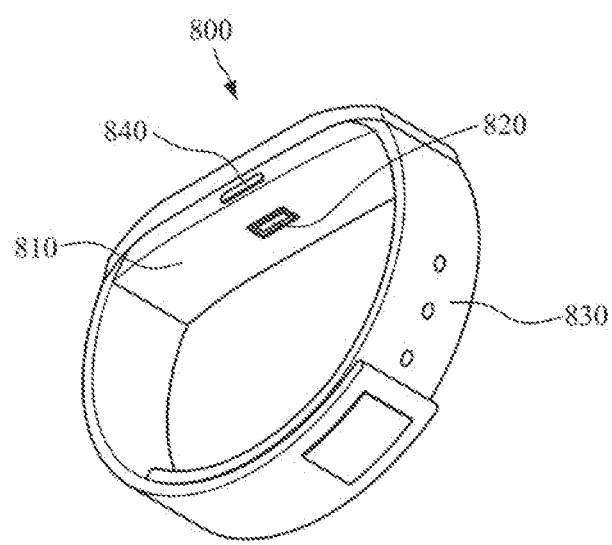
FIG. 8 is a diagram illustrating an example of a wearable device.

FIG. 8 is a diagram illustrating an example of a wearable device. The aforementioned embodiments of the apparatuses 100, 300a, and 300b for estimating bio-information may be mounted in the wearable device.

Referring to FIG. 8, the wearable device 800 includes a main body 810 and a strap 830.

The strap 830, which is connected to both ends of the main body 810, may be flexible so as to be wrapped around a user's wrist. The strap 830 may be composed of a first strap and a second strap which are separated from each other. Respective ends of the first strap and the second strap are connected to the main body 810, and the other ends thereof may be connected to each other via a connecting means. In this case, the connecting means may be formed as magnetic connection, Velcro connection, pin connection, and the like, but is not limited thereto. Further, the strap 830 is not limited thereto, and may be integrally formed as a non-detachable band.

In this case, air may be injected into the strap 830, or the strap 830 may be provided with an air bladder to have elasticity according to a change in pressure applied to the wrist, and may transmit the change in pressure of the wrist to the main body 810.

A battery may be embedded in the main body 810 or the strap 830 to supply power to the wearable device 800.

The main body 810 may include a sensor part 820 mounted on one side thereof. The sensor part 820 may include a pulse wave sensor for measuring pulse wave signals. The pulse wave sensor may include a light source for emitting light onto skin of a wrist or a finger, a light receiver, such as a contact image sensor (CIS) optical sensor, a photodiode, etc., which detects light scattered or reflected from the wrist or the finger. The pulse wave sensor may have multiple channels for measuring pulse wave signals at multiple points of the wrist, the finger, etc., and each of the channels may include a light source and a light receiver, or may include a plurality of light sources for emitting light of different wavelengths. In addition, the sensor part 820 may further include a force sensor for measuring a contact force between the wrist or finger and the sensor part 820.

A processor may be mounted in the main body 810. The processor may be electrically connected to modules mounted in the wearable device 800. The processor may obtain oscillograms based on the pulse wave signals and the contact force of each channel, which are measured by the sensor part 820, and may determine an optimal channel by using the obtained oscillograms. Further, the processor may estimate blood pressure by using the oscillogram of the determined optimal channel.

Further, the main body 810 may include a storage which stores reference information for estimating blood pressure and performing various functions of the wearable device 800, and information processed by various modules thereof.

In addition, the main body 810 may include a manipulator 840 which is provided on one side surface of the main body 810, and receives a user's control command and transmits the received control command to the processor. The manipulator 840 may have a power button to input a command to turn on/off the wearable device 800.

Further, a display for outputting information to a user may be mounted on a front surface of the main body 810. The display may have a touch screen for receiving touch input. The display may receive a user's touch input and transmit the touch input to the processor, and may display processing results of the processor.

Moreover, the main body 810 may include a communication interface for communication with an external device. The communication interface may transmit a blood pressure estimation result to the external device, e.g., a user's smartphone.

Figure 9:
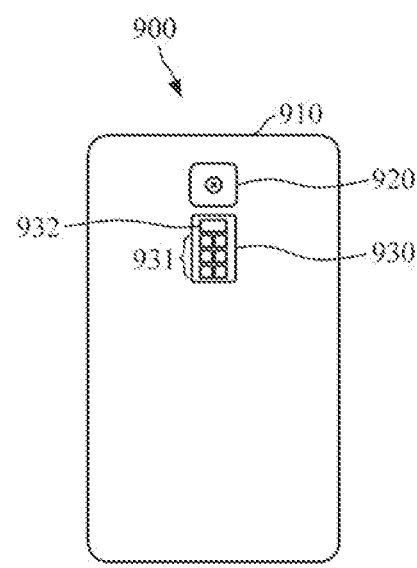
FIG. 9 is a diagram illustrating an example of a smart device.

FIG. 9 is a diagram illustrating an example of a smart device. In this case, the smart device may include a smartphone, a tablet PC, and the like. The smart device may include functions of the aforementioned apparatuses 100, 300a, and 300b for estimating bio-information.

Referring to FIG. 9, the smart device 900 includes a main body 910 and a pulse wave sensor 930 mounted on one surface of the main body 910. For example, the pulse wave sensor 930 may include one or more light sources 932 disposed at predetermined positions thereof. The one or more light sources 932 may emit light of different wavelengths. In addition, a plurality of light receivers 931 may be disposed at positions spaced apart from the light sources 932 by a predetermined distance. However, this is merely an example, and the pulse wave sensor 930 may have various shapes as described above. Further, a force sensor for measuring a contact force of a finger may be mounted in the main body 910 at a lower end of the pulse wave sensor 930.

Moreover, a display may be mounted on a front surface of the main body 910. The display may visually output a blood pressure estimation result, a health condition evaluation result, and the like. The display may include a touch screen, and may receive information input through the touch screen and transmit the information to a processor.

The main body 910 may include an image sensor 920 as illustrated in FIG. 9. The image sensor 920 may capture various images, and may acquire, for example, a fingerprint image of a finger being in contact with the pulse wave sensor 930. In addition, when an image sensor based on the CIS technology is mounted in the light receivers 931 of the pulse wave sensor 930, the image sensor 920 may be omitted.

As described above, the processor may obtain oscillograms based on the pulse wave signals measured by the pulse wave sensor 930, may determine an optimal channel based on the obtained oscillogram, and may estimate blood pressure based on the oscillogram of the determined optimal channel.

The example embodiments of the present disclosure can be implemented by computer-readable code written on a non-transitory computer-readable medium and executed by one or more processors. The non-transitory computer-readable medium may be any type of recording device in which data is stored in a non-transitory computer-readable manner.

Examples of the non-transitory computer-readable medium include a ROM, a RAM, a CD-ROM, a magnetic tape, a floppy disc, an optical data storage, and a carrier wave (e.g., data transmission through the Internet). The computer-readable medium can be distributed over a plurality of computer systems connected to a network so that computer-readable code is written thereto and executed therefrom in a decentralized manner. Functional programs, code, and code segments for implementing the example embodiments of the present disclosure can be deduced by programmers of ordinary skill in the art to which the disclosure pertains.

The present disclosure has been described herein with regard to example embodiments. However, it will be obvious to those skilled in the art that various changes and modifications can be made without changing technical conception of the present disclosure. Thus, it is clear that the above-described embodiments are illustrative in all aspects and are not intended to limit the present disclosure.

What is claimed is:

1. An apparatus for estimating bio-information, the apparatus comprising:
a pulse wave sensor including a plurality of channels, and configured to measure pulse wave signals at a plurality of points of an object; and
a processor configured to:
generate oscillograms corresponding to the plurality of channels based on the pulse wave signals measured by the plurality of channels;
determine a channel, from among the plurality of channels, for estimating the bio-information based on the oscillograms; and
estimate the bio-information based on an oscillogram of the channel, wherein the processor is further configured to:
exclude a channel, the excluded channel having an oscillogram which does not satisfy predetermined criteria;
wherein the excluded channel corresponding to the oscillogram is excluded when a full width at half maximum (FWHM) between a contact pressure at an onset point and a contact pressure at a half-maximum point of the oscillogram is greater than or equal to a predetermined threshold value, or a width at a point corresponding to a predetermined ratio between the onset point and the maximum point of the oscillogram is greater than or equal to a predetermined threshold value; and
determine the channel based on remaining oscillograms of remaining channels, wherein the processor is further configured to:
obtain a plurality of estimated mean arterial pressure (MAP) values respectively corresponding to the plurality of channels based on the oscillograms;
determine the channel based on the estimated MAP values; and
determine a predetermined number of channels in an order of magnitude of the MAP values.

2. The apparatus of claim 1, wherein the pulse wave sensor comprises:
a plurality of light sources configured to emit light onto the object; and
a plurality of light receivers respectively disposed at predetermined distances from the plurality of light sources, and configured to detect light scattered or reflected from the object.

3. The apparatus of claim 2, wherein the plurality of light receivers comprise at least one of a photodiode array and a complementary metal-oxide semiconductor (CMOS) image sensor.

4. The apparatus of claim 2, wherein in response to light of a plurality of wavelengths being emitted from each channel, the processor is further configured to generate the oscillograms by subtracting a second oscillogram for a second pulse wave signal of a second wavelength from a first oscillogram for a first pulse wave signal of a first wavelength.

5. The apparatus of claim 4, wherein the processor is further configured to:
determine a difference coefficient for the first wavelength and the second wavelength;
apply the difference coefficient to the second oscillogram; and
subtract the second oscillogram from the first oscillogram based on applying the difference coefficient to the second oscillogram.

6. The apparatus of claim 1, further comprising a force sensor configured to measure a contact force exerted between the object and the pulse wave sensor while the pulse wave signals are measured.

7. The apparatus of claim 6, further comprising an area sensor configured to measure a contact area when the object increases or decreases a pressing force applied to the pulse wave sensor.

8. The apparatus of claim 1, wherein the processor is further configured to control an output interface to output information that guides a contact pressure between the object and the pulse wave sensor while the pulse wave signals are measured.

9. The apparatus of claim 1, wherein the bio-information comprises one or more of blood pressure, vascular age, arterial stiffness, aortic pressure waveform, vascular compliance, stress index, fatigue level, skin age, and skin elasticity.

10. A method of estimating bio-information, the method comprising:
measuring, by a pulse wave sensor including a plurality of channels, pulse wave signals at a plurality of points of an object;
measuring, by a pressure sensor, an amount of pressure applied to the object;
using a processor to:
generate oscillograms corresponding to the plurality of channels based on the pulse wave signals measured by the plurality of channels;
determine a channel, from among the plurality of channels, for estimating the bio-information based on the oscillograms;
estimate the bio-information based on an oscillogram of the channel,
wherein the determining of the channel comprises excluding a channel, the excluded channel having an oscillogram which does not satisfy predetermined criteria, and determining the channel based on remaining oscillograms of remaining channels,
wherein the excluded channel corresponding to the oscillogram is excluded when a full width at half maximum (FWHM) between a contact pressure at an onset point and a contact pressure at a half-maximum point of the oscillogram is greater than or equal to a predetermined threshold value, or a width at a point corresponding to a predetermined ratio between the onset point and the maximum point of the oscillogram is greater than or equal to a predetermined threshold value; and
inform a user how to adjust placement of the pulse wave sensor based on an output of the pressure sensor,
and further using the processor to:
obtain a plurality of estimated mean arterial pressure (MAP) values respectively corresponding to the plurality of channels based on the oscillograms;
determine the channel based on the estimated MAP values; and
determine a predetermined number of channels in an order of magnitude of the MAP values.

11. The method of claim 10, wherein the generating of the oscillograms comprises, in response to light of a plurality of wavelengths being emitted from each channel, generating the oscillograms by subtracting a second oscillogram for a second pulse wave signal of a second wavelength from a first oscillogram for a first pulse wave signal of a first wavelength.

12. The method of claim 11, wherein the generating of the oscillograms comprises determining a difference coefficient for the first wavelength and the second wavelength, applying the difference coefficient to the second oscillogram, and subtracting the second oscillogram from the first oscillogram.

13. The method of claim 10, further comprising obtaining a contact pressure between the object and the pulse wave sensor while the pulse wave signals are measured.

* * * * *